(12) United States Patent
Abufarha et al.

(10) Patent No.: US 10,844,383 B1
(45) Date of Patent: Nov. 24, 2020

(54) MICRORNA DYSLIPIDEMIA INHIBITOR

(71) Applicant: DASMAN DIABETES INSTITUTE, Dasman (KW)

(72) Inventors: Mohamed Abufarha, Dasman (KW); Jehad Abubaker, Dasman (KW); Fahd Al Mulla, Dasman (KW); Preethi Cherian, Dasman (KW); Irina Alkhairi, Dasman (KW)

(73) Assignee: DASMAN DIABETES INSTITUTE, Dasman (KW)

( * ) Notice: Subject to any disclaimer, the term of this patent is extended or adjusted under 35 U.S.C. 154(b) by 0 days.

(21) Appl. No.: 16/574,617

(22) Filed: Sep. 18, 2019

(51) Int. Cl.
*C12N 15/113* (2010.01)

(52) U.S. Cl.
CPC .... *C12N 15/1136* (2013.01); *C12N 2310/141* (2013.01)

(58) Field of Classification Search
None
See application file for complete search history.

(56) References Cited

U.S. PATENT DOCUMENTS

| 8,288,356 B2 | 10/2012 | Obad et al. |
| 10,138,484 B2 | 11/2018 | Bhat et al. |
| 2017/0145519 A1* | 5/2017 | Park ................. C12Q 1/6886 |

FOREIGN PATENT DOCUMENTS

| WO | 2010133970 A1 | 11/2010 |
| WO | 2012072685 A1 | 6/2012 |

OTHER PUBLICATIONS

Trajkovski, M. et al., "MicroRNAs 103 and 107 regulate insulin sensitivity," Nature 474: pp. 649-653 (2011).
Chakraborty, C. et al., "Therapeutic miRNA and siRNA: Moving from Bench to Clinic as Next Generation Medicine," Mol. Therapy: Nucleic Acids 8: pp. 132-143 (2017).
Kirby, T. et al., "Integrative mRNA-microRNA analyses reveal novel interactions related to insulin sensitivity in human adipose tissue," Physiol. Genomics 48(2): pp. 145-153 (2015).
Mysore, R. et al., "MicroRNA-221-3p Regulates Angiopoietin-Like 8 (ANGPTL8) Expression in Adipocytes," J. Clin. Endocrinol. Metab. 102(11): pp. 4001-4012 (2017).
Aranda, J. F. et al., "MicroRNA modulation of lipid metabolism and oxidative stress in cardiometabolic disease," Free Radic. Biol. Med. 64: pp. 31-39 (2013).

* cited by examiner

*Primary Examiner* — Tracy Vivlemore
(74) *Attorney, Agent, or Firm* — Nath, Goldberg & Meyer; Richard C. Litman

(57) ABSTRACT

The microRNA dyslipidemia inhibitor includes methods of administering a miRNA capable of inhibiting dyslipidemia to a subject in need thereof. The methods of the miRNA dyslipidemia inhibitor may include administration of miRNA-103 to a subject in need thereof. The administration of miRNA-103 may inhibit ANGPTL8 activity, thereby reducing ANGPTL8's inhibition of lipoprotein lipase activity and increasing triglyceride degradation. The administration of miRNA-103 may be used to treat or prevent lipid metabolism disorders including dyslipidemia and dyslipidemia associated diseases, such as hyperlipidemia, atherosclerosis, heart disease, and the like.

9 Claims, 5 Drawing Sheets
Specification includes a Sequence Listing.

SEQUENCE LISTING

```
<160> NUMBER OF SEQ ID NOS: 5

<210> SEQ ID NO 1
<211> LENGTH: 78
<212> TYPE: RNA
<213> ORGANISM: Homo sapiens

<400> SEQUENCE: 1
uacugcccuc ggcuucuuua cagugcugcc uuguugcaua uggaucaagc agcauuguac    60
agggcuauga aggcauug                                                  78

<210> SEQ ID NO 2
<211> LENGTH: 23
<212> TYPE: RNA
<213> ORGANISM: Homo sapiens

<400> SEQUENCE: 2
agcagcauug uacagggcua uga                                            23

<210> SEQ ID NO 3
<211> LENGTH: 36
<212> TYPE: RNA
<213> ORGANISM: Homo sapiens

<400> SEQUENCE: 3
ggauggaacu gaggaccaau caugcugcaa ggaaca                              36

<210> SEQ ID NO 4
<211> LENGTH: 36
<212> TYPE: RNA
<213> ORGANISM: Pan troglodytes

<400> SEQUENCE: 4
ggauggaacu gaggaccaau caugcugcaa ggagca                              36

<210> SEQ ID NO 5
<211> LENGTH: 36
<212> TYPE: RNA
<213> ORGANISM: Macaca mulatta

<400> SEQUENCE: 5
ggauggaacu gaggaccaac caugcugcaa ggaaca                              36
```

MICRORNA DYSLIPIDEMIA INHIBITOR

INCORPORATION BY REFERENCE OF MATERIAL SUBMITTED IN COMPUTER READABLE FORM

The Applicants hereby incorporate by reference the sequence listing contained in the ASCII text filed titled 33024_01_sequence_listing_ST25.txt, created Jul. 16, 2019, and having 1 KB of data.

BACKGROUND

1. Field

The disclosure of the present patent application relates to dyslipidemia, and particularly to a microRNA dyslipidemia inhibitor.

2. Description of the Related Art

Dyslipidemia is characterized by the presence of an abnormal amount of one or more lipids in the blood of a subject. The lipids may include but are not limited to triglycerides, cholesterol (including low-density lipoproteins (LDL) and high-density lipoproteins (HDL)), fat phospholipids, and a combination thereof. Dyslipidemia may be caused by a number of factors, including but not limited to diet, lifestyle, prolonged elevated insulin levels, elevated levels of O-linked N-acetylglucosamine transferace (OGT), and a combination thereof. While dyslipidemia includes abnormally high or abnormally low lipid profiles, the most common forms involve one or more of high levels of LDL, low levels of HDL, high levels of triglycerides, and a combination thereof.

Subjects suffering from dyslipidemia involving elevated LDL and elevated triglycerides or low HDL levels are at risk of developing atherosclerosis, or buildup of hard, fatty deposits (plaques) within the blood vessels. Atherosclerosis increases the difficulty of blood flow, and thus can lead to heart attacks or strokes. Demand for pharmaceuticals to address dyslipidemia is increasing, and current treatments for this disorder are among some of the most widely prescribed medications in the world.

Current treatments for dyslipidemia include statins and fibrates. Statins act by blocking cholesterol synthesis in the liver, thereby lowering LDL levels in the blood. Statins have numerous well reported side effects, including muscle pain, increased risk of developing diabetes, and liver damage. Fibrates increase HDL levels and lower triglyceride levels in the blood stream. Common side effects of fibrates include stomach upset, muscle pain, and gallstones. As each individual responds to these drugs differently, there is a desire to develop new classes of anti-dyslipidemia pharmaceuticals.

MicroRNAs (miRNAs) are small (approximately 18-24 nucleotides in length), non-coding, RNA molecules encoded in the genomes of plants, animals, and some viruses. MiRNAs function via base-pairing with complementary sequences within messenger RNA (mRNA) molecules, and may act through RNA silencing or post-transcriptional regulation of gene expression. In certain instances, highly conserved, endogenously expressed miRNAs regulate the expression of genes by binding to the 3'-untranslated regions (3'-UTR) of specific mRNAs. More than 1000 different miRNAs have been identified. Some mature miRNAs appear to originate from long (frequently hundreds of nucleotides) endogenous primary miRNA transcripts (pri-miRNAs).

Functional analyses of miRNAs have demonstrated that they contribute to different physiological processes in animals, including developmental timing, organogenesis, differentiation, patterning, embryogenesis, growth control and programmed cell death. Examples of particular processes in which miRNAs participate include stem cell differentiation, neurogenesis, angiogenesis, hematopoiesis, and exocytosis.

Recently, the first targeted RNA based therapy was approved for the treatment of polyneuropathy caused by hereditary transthyretin-mediated amyloidosis. However, to date no RNA based therapies for the treatment of dyslipidemia have yet to be developed.

Thus, a miRNA dyslipidemia inhibitor solving the aforementioned problems is desired.

SUMMARY

The present subject matter relates to methods of administering a miRNA capable of inhibiting dyslipidemia to a subject in need thereof. The methods of administering the miRNA dyslipidemia inhibitor may include administration of miRNA-103 to a subject in need thereof. The administration of miRNA-103 may inhibit ANGPTL8 activity, thereby reducing ANGPTL8's inhibition of lipoprotein lipase activity and increasing triglyceride degradation. The administration of miRNA-103 may be used to treat or prevent lipid metabolism disorders including dyslipidemia and dyslipidemia associated diseases, such as hyperlipidemia, atherosclerosis, heart disease, and the like.

These and other features of the present disclosure will become readily apparent upon further review of the following specification and drawings.

DETAILED DESCRIPTION OF THE PREFERRED EMBODIMENTS

The present methods relate to methods of administering a miRNA capable of inhibiting dyslipidemia to a subject in need thereof. The methods may include administration of miRNA-103 to a subject in need thereof. The administration of miRNA-103 may inhibit ANGPTL8 activity, thereby reducing ANGPTL8's inhibition of lipoprotein lipase activity and increasing triglyceride degradation. The administration of miRNA-103 may be used to treat or prevent lipid metabolism disorders including dyslipidemia and dyslipidemia associated diseases, such as hyperlipidemia, atherosclerosis, heart disease, and the like.

Figure 1:
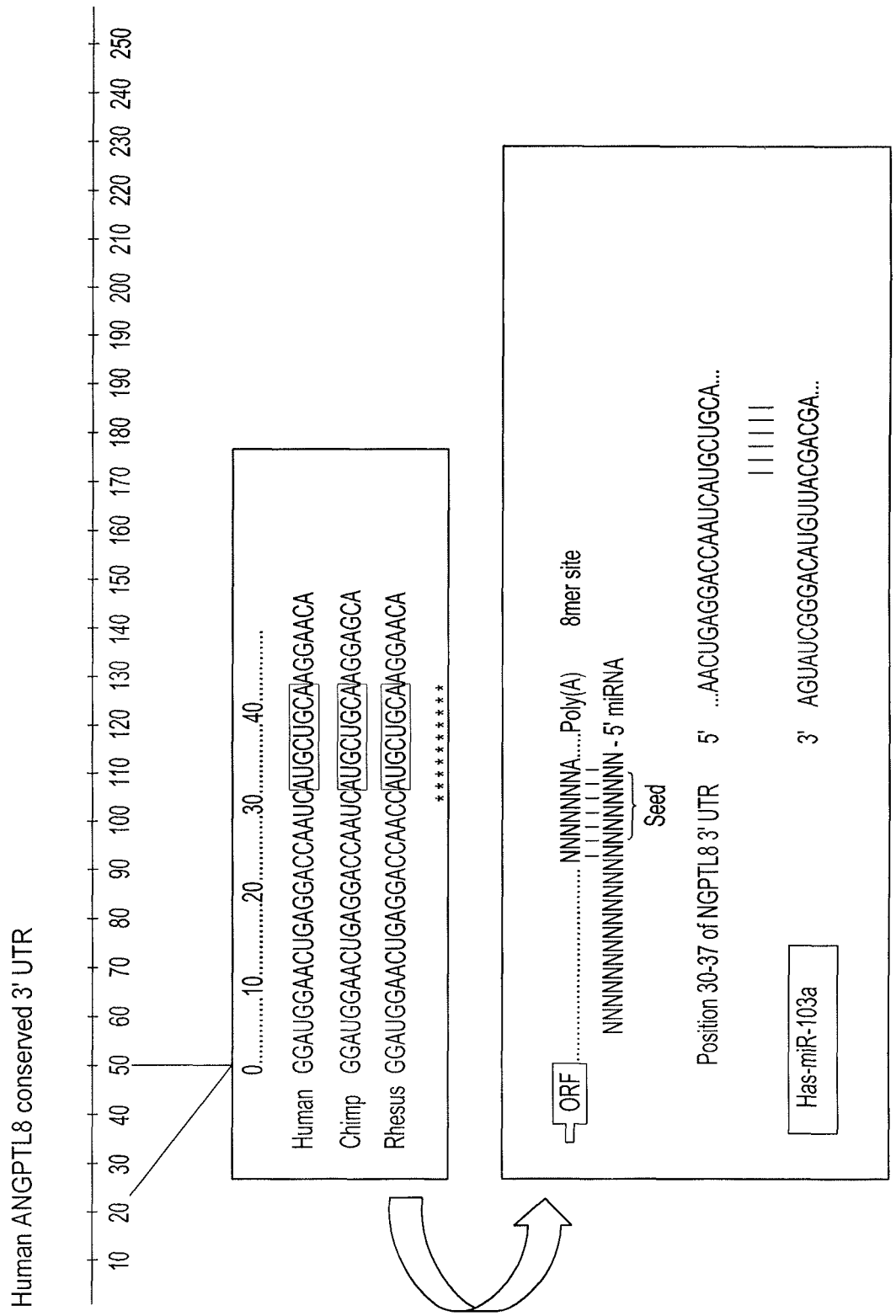
FIG. 1 depicts a bioinformatics prediction aligning miRNA-103 and the 3'UTR of human ANGPTL8 (SEQ ID NO: 3) with the 3'UTR of Chimpanzee ANGPTL8 (SEQ ID NO: 4) and the 3'UTR of Rhesus ANGPTL8 (SEQ ID NO: 5), illustrating the conserved binding site for miRNA-103 (SEQ ID NO: 2) aligned to position 30-37 of the Human ANGPTL8 3'UTR (SEQ ID NO: 3).
Figure 5:
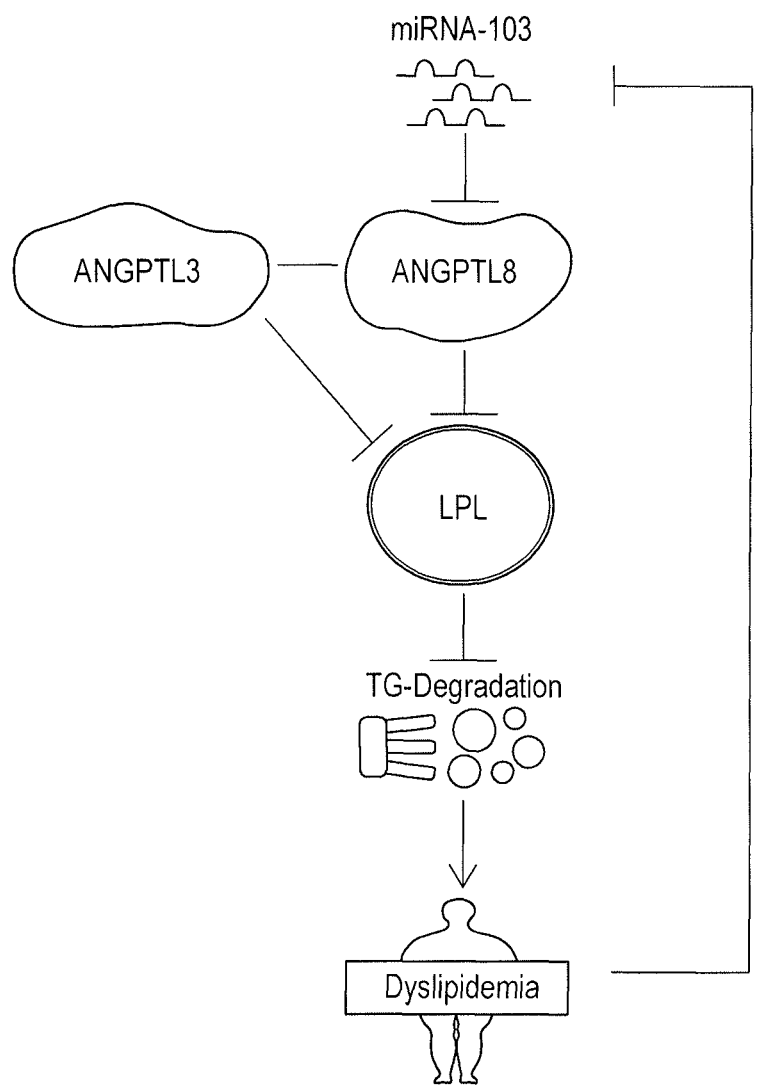
FIG. 5 depicts a proposed model for miRNA-103 repression of ANGPTL8 expression, thereby reducing ANGPTL8 inhibition of lipoprotein lipase activity, resulting in increased triglyceride degradation and reducing dyslipidemia.

As illustrated in FIG. 5, ANGPTL8 is known to inhibit lipoprotein lipase (LPL) activity, which may in turn interfere with LPL-mediated hydrolysis of triglycerides in the blood stream (triglyceride degradation). Thus, inhibiting ANGPTL8 may increase LPL activity and thus triglyceride degradation. As illustrated in FIG. 1, miRNA-103 aligns with the 3'UTR and is predicted to interfere with ANGPTL8 expression. This prediction was confirmed by experimental results reflected in FIGS. 4A-4E, which briefly illustrate a negative correlation between miRNA-103 levels in circulating blood and a subject's obesity index, body mass index, and circulating Leptin and triglyceride levels, as well as a positive correlation between ANGPTL8 levels in circulating blood and a subject's obesity index. Thus, the administration of miRNA-103 is confirmed to reduce circulating triglyceride levels, and to be an effective treatment to prevent dyslipidemia associated diseases and risk factors, including obesity and increased body mass index.

I. Definitions

The term "miRNA" is used herein according to its ordinary and plain meaning and refers to a microRNA molecule found in eukaryotes that is involved in RNA-based gene regulation. The term will be used to refer to the single-stranded RNA molecule processed from a precursor. Names of miRNAs and their sequences related to a miRNA dyslipidemia inhibitor are provided herein. The term miRNA generally refers to a single-stranded molecule, but in specific embodiments, miRNA may also encompass molecules having a region or an additional strand that is partially (between 10 and 50% complementary across the length of strand), substantially (greater than 50% but less than 100% complementary across the length of strand) or fully complementary to another region of the same single-stranded molecule or to another nucleic acid. Thus, miRNA nucleic acids may encompass a molecule that comprises one or more complementary or self-complementary strand(s) or "complement(s)" of a particular sequence. For example, precursor miRNA may have a self-complementary region, which is up to 100% complementary. miRNA probes or nucleic acids can include, can be or can be at least 60, 65, 70, 75, 80, 85, 90, 95, 96, 97, 98, 99 or 100% complementary to their target.

The term "mRNA" is used herein according to its ordinary and plain meaning and refers to a messenger RNA molecule typically understood to convey genetic information copied from DNA to the ribosome, where the mRNA sequence is translated to produce a protein from individual amino acids. The term will be used to refer to the single-stranded RNA molecule processed from a precursor.

The use of the word "a" or "an" when used herein in conjunction with the term "comprising" in the claims and/or the specification may mean "one," but it is also consistent with the meaning of "one or more," "at least one," and "one or more than one."

Throughout this application, the term "about" may be used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In certain cases, the term "comprising" may be replaced with "consisting essentially of" or "consisting of."

The term "recombinant" is generally used herein to refer to a molecule that has been manipulated in vitro or that is a replicated or expressed product of such a molecule.

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid."

As used herein, the term "synthetic nucleic acid" means that the nucleic acid does not have all or part of a chemical structure or sequence of a naturally occurring nucleic acid or was made by man and not a biologic cell or organism. Consequently, it will be understood that the term "synthetic miRNA" refers to a nucleic acid that functions in a cell or under physiological conditions in the same manner as a naturally occurring miRNA.

The term "complementary region" or "complement" as used herein refers to a region of a nucleic acid or mimetic that is or is at least 60% complementary to the mature, naturally occurring miRNA sequence. The complementary region can be at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9 or 100% complementary including all values and ranges there between. With single polynucleotide sequences, there may be a hairpin loop structure as a result of chemical bonding between the miRNA region and the complementary region. In other embodiments, the complementary region is on a different nucleic acid molecule than the miRNA region, in which case the complementary region is on the complementary strand and the miRNA region is on the active strand.

The term "isolated" as used herein means that the "isolated" nucleic acid molecules are initially separated from different (in terms of sequence or structure) and unwanted nucleic acid molecules such that a population of isolated nucleic acids is at least about 90% homogenous, and may be at least about 95, 96, 97, 98, 99, or 100% homogenous with respect to other polynucleotide molecules. In many embodiments, a nucleic acid is isolated by virtue of it having been synthesized in vitro separate from endogenous nucleic acids in a cell. It will be understood, however, that isolated nucleic acids may be subsequently mixed or pooled together. In certain aspects, the synthetic miRNA are RNA or RNA analogs. miRNA inhibitors may be DNA or RNA, or analogs thereof.

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in a manner that may substitute for naturally occurring nucleobase pairing (e.g., the hydrogen bonding between A and T, G and C, and A and U).

As used herein, the terms "purine" and/or "pyrimidine" nucleobase(s) encompass naturally occurring purine and/or pyrimidine nucleobases and also derivative(s) and analog(s) thereof, including but not limited to, those having a purine or pyrimidine substituted by one or more of an alkyl, carboxyalkyl, amino, hydroxyl, halogen (i.e., fluoro, chloro, bromo, or iodo), thiol or alkylthiol moiety. Preferred alkyl (e.g., alkyl, carboxyalkyl, etc.) moieties comprise from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

As used herein, a "nucleoside" refers to an individual chemical unit comprising a nucleobase covalently attached to a nucleobase linker moiety.

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

The phrase "pharmaceutically acceptable" as used herein refers to molecular entities and compositions that do not produce an allergic or similar untoward reaction when administered to a human.

The term "subject" as used herein, means a mammal, including but not limited to a human being.

The term "non-synthetic" in the context of miRNA as used herein means that the miRNA is not "synthetic," as defined herein. Furthermore, it is contemplated that in embodiments of a miRNA dyslipidemia inhibitor that concern the use of synthetic miRNAs, the use of corresponding non-synthetic miRNAs is also considered an aspect of a miRNA dyslipidemia inhibitor, and vice versa.

As used herein, the term "providing" an agent is used to include "administering" the agent to a patient.

As used herein, a "carrier" includes any and all solvents, dispersion media, vehicles, coatings, diluents, isotonic and absorption delaying agents, buffers, carrier solutions, suspensions, colloids, excipients, and the like.

As used herein, the term "naturally occurring" refers to something found in an organism without any intervention by a person; it could refer to a naturally-occurring wildtype or mutant molecule. In some embodiments a synthetic miRNA molecule does not have the sequence of a naturally occurring miRNA molecule. In other embodiments, a synthetic miRNA molecule may have the sequence of a naturally occurring miRNA molecule, but the chemical structure of the molecule, particularly in the part unrelated specifically to the precise sequence (non-sequence chemical structure) differs from the chemical structure of the naturally occurring miRNA molecule with that sequence. In some cases, the synthetic miRNA has both a sequence and non-sequence chemical structure that are not found in a naturally-occurring miRNA. Moreover, the sequence of the synthetic molecules will identify which miRNA is effectively being provided; the endogenous miRNA will be referred to as the "corresponding miRNA." Corresponding miRNA sequences that can be used in the context of a miRNA dyslipidemia inhibitor include, but are not limited to, all or a portion of those sequences in the SEQ IDs provided herein, as well as any other miRNA sequence, miRNA precursor sequence, or any sequence complementary thereof. In some embodiments, the sequence is or is derived from or contains all or part of a sequence identified herein to target a particular miRNA (or set of miRNAs) that can be used with that sequence. Any 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130 140, 150, 160, 170, 180, 190, 200, 210, 220, 230, 240, 250, 260 or any number or range of sequences there between may be selected to the exclusion of all non-selected sequences.

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art.

A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring. Different types of covalent attachment(s) of a nucleobase to a nucleobase linker moiety are known in the art.

II. Nucleic Acids

The miRNA dyslipidemia inhibitor contemplated herein may include nucleic acids, modified nucleic acids, nucleic acid mimetics, miRNAs, and segments thereof that can be employed in therapeutic applications, particularly those applications related to pathological conditions. These molecules may have been endogenously produced by a cell and isolated, or synthesized, or produced chemically or recombinantly. They may be isolated and/or purified. Each of the miRNAs described herein includes the corresponding SEQ ID NO and accession numbers for these miRNA sequences. The name of a miRNA is often abbreviated and referred to without a "hsa-" prefix and will be understood as such, depending on the context. Unless otherwise indicated, miRNAs referred to in the application are human sequences identified as miR-X or let-X, where X is a number and/or letter.

In certain aspects, a miRNA designated by a suffix "5P" or "3P" can be used. "5P" indicates that the mature miRNA derives from the 5' end of the precursor and a corresponding "3P" indicates that it derives from the 3' end of the precursor. Moreover, in some embodiments, a miRNA probe is used that does not correspond to a known human miRNA. It is contemplated that these non-human miRNA probes may be used in embodiments of a miRNA dyslipidemia inhibitor or that there may exist a human miRNA that is homologous to the non-human miRNA. In other embodiments, any mammalian cell, biological sample, or preparation thereof may be employed.

The miRNA dyslipidemia inhibitor may include, in some embodiments, short nucleic acid molecules that function as miRNAs in a cell. The term "short" refers to a length of a single polynucleotide that is at least, at most, or about 6, 7, 8, 9, 10, 11, 12, 13, 14, 15, 16, 17, 18, 19, 20, 21, 22, 23, 24, or 25 nucleotides, including all integers or ranges derivable there between. The nucleic acid molecules are typically synthetic nucleic acids. In certain aspects the sequence (the entire sequence) and/or chemical structure deviates from a naturally-occurring nucleic acid molecule, such as an endogenous precursor miRNA or miRNA molecule or complement thereof. While in some embodiments, nucleic acids of a miRNA dyslipidemia inhibitor do not have an entire sequence that is identical or complementary to a sequence of a naturally-occurring nucleic acid, such molecules may encompass all or part of a naturally-occurring sequence or a complement thereof. It is contemplated, however, that a synthetic nucleic acid administered to a cell may subsequently be modified or altered in the cell such that its structure or sequence is the same as non-synthetic or naturally occurring nucleic acid, such as a mature miRNA sequence. For example, a synthetic nucleic acid may have a sequence that differs from the sequence of a precursor miRNA, but that sequence may be altered once in a cell to be the same as an endogenous, processed miRNA or an inhibitor thereof.

In some embodiments, the present subject matter relates to a miRNA or a synthetic miRNA having a length of between 10 and 200 residues. The miRNA dyslipidemia inhibitor herein may include miRNA or synthetic miRNA molecules that are, are at least, or are at most 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 140, 145, 150, 160, 170, 180, 190, 200 or more residues in length, including any integer or any range there between.

In certain embodiments, synthetic miRNA have (a) a "miRNA region" whose sequence or binding region from 5' to 3' is identical or complementary to all or a segment of a mature miRNA sequence, and (b) a "complementary region" whose sequence from 5' to 3' is between 60% and 100% complementary to the miRNA sequence in (a). In certain embodiments, these synthetic miRNA are also isolated, as defined above. The term "miRNA region" or complement thereof refers to a region on the synthetic miRNA that is at least 75, 80, 85, 90, 95, or 100% identical, including all integers there between, to the entire sequence of a mature, naturally occurring miRNA sequence or a complement thereof. In certain embodiments, the miRNA region is or is at least 90, 91, 92, 93, 94, 95, 96, 97, 98, 99, 99.1, 99.2, 99.3, 99.4, 99.5, 99.6, 99.7, 99.8, 99.9 or 100% identical to the sequence of a naturally-occurring miRNA or complement thereof. In certain aspects, a double stranded RNA can comprise a miRNA sequence that is 90 to 100% identical to sequences described herein, as described directly above, and a second nucleic acid that is complementary to the miRNA sequence and is 60, 65, 70, 75, 80, 85, 90, 95, or 100% identical, including all integers there between, to the miRNA sequence.

In some embodiments of a miRNA dyslipidemia inhibitor a synthetic miRNA contains one or more design element(s). These design elements include, but are not limited to: (i) a replacement group for the phosphate or hydroxyl of the nucleotide at the 5' terminus of the complementary region; (ii) one or more sugar modifications in the first or last 1 to 6 residues of the complementary region; or, (iii) noncomplementarity between one or more nucleotides in the last 1 to 5 residues at the 3' end of the complementary region and the corresponding nucleotides of the miRNA region. A variety of design modifications are known in the art, see below.

In certain embodiments, a synthetic miRNA has a nucleotide at its 5' end of the complementary region in which the phosphate and/or hydroxyl group has been replaced with another chemical group (referred to as the "replacement design"). In some cases, the phosphate group is replaced, while in others, the hydroxyl group has been replaced. In particular embodiments, the replacement group is biotin, an amine group, a lower alkylamine group, an acetyl group, 2'O-Me (2' oxygen-methyl), DMTO (4,4'-dimethoxytrityl with oxygen), fluorescein, a thiol, or acridine, though other replacement groups are well known to those of skill in the art and can be used as well. This design element can also be used with a miRNA inhibitor.

Additional embodiments concern a synthetic miRNA having one or more sugar modifications in the first or last 1 to 6 residues of the complementary region (referred to as the "sugar replacement design"). In certain cases, there are one or more sugar modifications in the first 1, 2, 3, 4, 5, 6 or more residues of the complementary region, or any range derivable therein. In additional cases, there are one or more sugar modifications in the last 1, 2, 3, 4, 5, 6 or more residues of the complementary region, or any range derivable therein, have a sugar modification, with the understanding that such modifications must be in the complementary region only. It will be understood that the terms "first" and "last" are with respect to the order of residues from the 5' end to the 3' end of the region. In particular embodiments, the sugar modification is a 2'O-Me modification, a 2'F modification, a 2'H modification, a 2' amino modification, a 4'thioribose modification or a phosphorothioate modification on the carboxy group linked to the carbon at position 6'. In further embodiments, there are one or more sugar modifications in the first or last 2 to 4 residues of the complementary region or the first or last 4 to 6 residues of the complementary region. This design element can also be used with a miRNA inhibitor. Thus, a miRNA inhibitor can have this design element and/or a replacement group on the nucleotide at the 5' terminus, as discussed above.

In other embodiments of the present miRNA dyslipidemia inhibitor, there is a synthetic miRNA in which one or more nucleotides in the last 1 to 5 residues at the 3' end of the complementary region are not complementary to the corresponding nucleotides of the miRNA region ("noncomplementarity") (referred to as the "noncomplementarity design"). The noncomplementarity may be in the last 1, 2, 3, 4, and/or 5 residues of the complementary miRNA. In certain embodiments, there is noncomplementarity with at least 2 nucleotides in the complementary region.

It is contemplated that synthetic miRNA of the present miRNA dyslipidemia inhibitor may have one or more of the replacement, sugar modification, or noncomplementarity designs. In certain cases, synthetic RNA molecules have two of them, while in others these molecules have all three designs in place.

The miRNA region and the complementary region may be on the same or separate polynucleotides. In cases in which they are contained on or in the same polynucleotide, the miRNA molecule will be considered a single polynucleotide. In embodiments in which the different regions are on separate polynucleotides, the synthetic miRNA will be considered to be comprised of two polynucleotides.

When the RNA molecule is a single polynucleotide, there can be a linker region between the miRNA region and the complementary region. In some embodiments, the single polynucleotide is capable of forming a hairpin loop structure as a result of bonding between the miRNA region and the complementary region. The linker constitutes the hairpin loop. It is contemplated that in some embodiments, the linker region is, is at least, or is at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 residues in length, or any range derivable therein. In certain embodiments, the linker is between 3 and 30 residues (inclusive) in length.

In addition to having a miRNA region and a complementary region, there may be flanking sequences as well at either the 5' or 3' end of the region. In some embodiments, there is or is at least 1, 2, 3, 4, 5, 6, 7, 8, 9, 10 nucleotides or more, or any range derivable therein, flanking one or both sides of these regions.

In some embodiments herein, methods and compositions involving miRNA may concern nucleic acids comprising miRNA nucleotide sequences. Nucleic acids may be, be at least, or be at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides, or any range derivable therein, in length. Such lengths cover the lengths of processed miRNA, precursor miRNA, miRNA containing vectors, and therapeutic miRNA. In many embodiments, miRNA are 14-35 nucleotides in length. miRNA precursors are generally between 62 and 110 nucleotides in humans.

In some embodiments, the miRNA is miRNA-103. The miRNA may include sequences that are between 80% and 100% or that are 80%, 85%, 90%, 95%, or 100% complementary to at least one of the miRNA-103 precursor sequence: UACUGCCCUCGGCUUCUUUACA-GUGCUGCCUUGUUGCAUAUGGAUCAAGCAGC AUUGUACAGGGCUAUGAAGGCAUUG (SEQ ID NO. 1), or the miRNA-103 mature sequence: AGCAGCAUU-GUACAGGGCUAUGA (SEQ ID NO. 2).

It is understood that some nucleic acids are derived from genomic sequences or a gene. In this respect, the term "gene" is used for simplicity to refer to the genomic sequence encoding the precursor nucleic acid or miRNA for a given miRNA. However, in some embodiments the gene of a given miRNA may include further sequences that are involved in its expression, such as a promoter or other regulatory sequences.

While embodiments of a miRNA dyslipidemia inhibitor may involve synthetic miRNAs or synthetic nucleic acids, in some embodiments of a miRNA dyslipidemia inhibitor, the nucleic acid molecule(s) need not be "synthetic." In certain embodiments, a non-synthetic nucleic acid or miRNA employed in methods and compositions of a miRNA dyslipidemia inhibitor may have the entire sequence and structure of a naturally occurring mRNA or miRNA precursor or the mature mRNA or miRNA. For example, non-synthetic miRNAs used in methods and compositions of a miRNA dyslipidemia inhibitor may not have one or more modified nucleotides or nucleotide analogs. In these embodiments, the non-synthetic miRNA may or may not be recombinantly produced. In particular embodiments, the nucleic acid in methods and/or compositions of a miRNA dyslipidemia inhibitor is specifically a synthetic miRNA and not a non-synthetic miRNA (that is, not a miRNA that qualifies as "synthetic"); though in other embodiments, a miRNA dyslipidemia inhibitor specifically involves a non-synthetic miRNA and not a synthetic miRNA. Any embodiments discussed with respect to the use of synthetic miRNAs can be applied with respect to non-synthetic miRNAs, and vice versa.

Labeling methods and kits of a miRNA dyslipidemia inhibitor specifically contemplate the use of nucleotides that are both modified for attachment of a label and can be incorporated into a miRNA molecule. Such nucleotides include those that can be labeled with a dye, including a fluorescent dye, or with a molecule such as biotin. Labeled nucleotides are readily available; they can be acquired commercially or they can be synthesized by reactions known to those of skill in the art.

Modified nucleotides for use in a miRNA dyslipidemia inhibitor are not naturally occurring nucleotides, but instead, refer to prepared nucleotides that have a reactive moiety on them. Specific reactive functionalities of interest include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the other such chemical groups. In some embodiments, the reactive functionality may be bonded directly to a nucleotide, or it may be bonded to the nucleotide through a linking group. The functional moiety and any linker cannot substantially impair the ability of the nucleotide to be added to the miRNA or to be labeled. Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of particular interest in many embodiments is alkyl linking groups, typically lower alkyl linking groups of 1 to 16, usually 1 to 4 carbon atoms, where the linking groups may include one or more sites of unsaturation. The functionalized nucleotides (or primers) used in the above methods of functionalized target generation may be fabricated using known protocols or purchased from commercial vendors. Functional groups may be prepared according to methods known to those of skill in the art.

Preparation of Nucleic Acids

A nucleic acid may be made by any technique known to one of ordinary skill in the art, such as for example, chemical synthesis, enzymatic production, or biological production. It is specifically contemplated that the miRNA probes are chemically synthesized.

In some embodiments of a miRNA dyslipidemia inhibitor, miRNAs are recovered or isolated from a biological sample. The miRNA may be recombinant or it may be natural or endogenous to the cell. It is contemplated that a biological sample may be treated in a way so as to enhance the recovery of small RNA molecules such as miRNA. Generally, such methods may involve lysing cells with a solution having guanidinium and a detergent.

Alternatively, nucleic acid synthesis is performed according to standard methods known to those of skill in the art. Non-limiting examples of a synthetic nucleic acid (e.g., a synthetic oligonucleotide), include a nucleic acid made by in vitro chemical synthesis using phosphotriester, phosphite, or phosphoramidite chemistry and solid phase techniques, or via deoxynucleoside H-phosphonate intermediates.

A non-limiting example of an enzymatically produced nucleic acid may include one produced by enzymes in amplification reactions such as PCR. Oligonucleotide synthesis is well known to those of skill in the art.

Recombinant methods for producing nucleic acids in a cell are well known to those of skill in the art. These include the use of vectors (viral and non-viral), plasmids, cosmids, and other vehicles for delivering a nucleic acid to a cell, which may be the target cell (e.g., a cancer cell) or simply a host cell (to produce large quantities of the desired RNA molecule). The existing cellular machinery may then be used to transcribe nucleic acid sequences based upon the vector, plasmid, cosmid, or other vehicle template sequences. Alternatively, such vehicles can be used in the context of a cell free system so long as the reagents for generating the RNA molecule are present.

III. Treatment Options

Compositions and methods of the present subject matter can be used to inhibit dyslipidemia. Accordingly, the present methods contemplate using miRNA or one or more miRNA inhibitors for treating a variety of diseases with a dyslipidemia component (hereinafter collectively referred to as "lipid metabolism disorders"). In an embodiment, the present subject matter provides a method of treating dyslipidemid diseases in a subject comprising administration of an effective amount of a miRNA or a miRNA inhibitor to the subject.

The present methods may include supplying or enhancing the activity of one or more miRNAs in a cell. The miRNA dyslipidemia inhibitor may include inducing certain cellular characteristics by providing to a cell a particular nucleic acid, such as a specific synthetic miRNA molecule. However, in the present methods, the miRNA molecule or miRNA inhibitor need not be synthetic. They may have a sequence that is identical to a naturally occurring miRNA or they may not have any design modifications. In certain embodiments, the miRNA molecule is synthetic, as discussed herein.

The particular nucleic acid molecule provided to the cell is understood to correspond to a particular miRNA in the cell, and thus, the miRNA in the cell is referred to as the "corresponding miRNA." In situations in which a named miRNA molecule is introduced into a cell, the corresponding miRNA will be understood to be the induced or inhibited miRNA or induced or inhibited miRNA function. It is contemplated, however, that the miRNA molecule introduced into a cell is not a mature miRNA but is capable of becoming or functioning as a mature miRNA under the appropriate physiological conditions. It is contemplated that multiple corresponding miRNAs may be involved. Also, it will be understood that an amount of a synthetic nucleic acid that is provided to a cell or organism is an "effective amount" or "amount sufficient" for a particular result, which refers to an amount needed (or a sufficient amount) to achieve a desired goal, such as inducing a particular cellular characteristic(s), inhibiting ANGPTL8 activity or stimulating triglyceride degradation. In certain embodiments, the present methods include providing or introducing to a cell a nucleic acid molecule corresponding to a mature miRNA in the cell in an amount effective to achieve a desired physiological result. Moreover, methods can involve providing synthetic or non-synthetic miRNA molecules. Furthermore, any method articulated using a list of miRNAs using Markush group language may be articulated without the Markush group language and a disjunctive article (i.e., or) instead, and vice versa.

In some embodiments, a method for reducing or inhibiting dyslipidemia comprises introducing into or providing a subject, tissue, or cell an effective amount of a synthetic or non-synthetic miRNA molecule that corresponds to a miRNA sequence disclosed herein, or a complement or inhibitor thereof.

Certain embodiments herein include methods of treating a dyslipidemia disease. In one aspect, the method comprises contacting a target cell with one or more nucleic acid, synthetic miRNA, or miRNA comprising at least one nucleic acid segment having all or a portion of a miRNA sequence. The segment may be 5, 6, 7, 8, 9, 10, 11, 12, 13, 14, 15, 16, 17, 18, 19, 20, 21, 22, 23, 24, 25, 30 or more nucleotides or nucleotide analogs including all integers there between. In certain aspects, one or more nucleotides of the nucleic acid segment can be modified. An aspect of a miRNA dyslipidemia inhibitor includes the modulation of gene expression, miRNA expression or function, or mRNA expression or function within a target subject, tissue, or cell.

Typically, an endogenous gene, miRNA or mRNA is modulated in the cell. In particular embodiments, the nucleic acid sequence comprises at least one segment that is at least 70, 75, 80, 85, 90, 95, 96, 97, 98, 99, or 100% identical in nucleic acid sequence to one or more target miRNA or gene sequences. Modulation of the expression or processing of an endogenous gene, miRNA, or mRNA can be through modulation of the processing of an mRNA, such processing including transcription, transportation and/or translation in a cell. Modulation may also be effected by the inhibition or enhancement of miRNA activity in a cell, tissue, or organ. Such processing may affect the expression of an encoded product or the stability of the mRNA. In still other embodiments, a nucleic acid sequence can comprise a modified nucleic acid sequence. In certain aspects, one or more miRNA sequence may include or comprise a modified nucleobase or nucleic acid sequence.

It will be understood in the present methods that a cell or other biological matter such as an organism (including patients or subjects) can be provided with a miRNA or miRNA molecule corresponding to a particular miRNA by administering to the cell or organism a nucleic acid molecule that functions as the corresponding miRNA once inside the cell. In certain embodiments, it is specifically contemplated that the miRNA molecule provided to the biological matter is not a mature miRNA molecule but a nucleic acid molecule that can be processed into the mature miRNA once it is accessible to miRNA processing machinery.

In certain methods of using a miRNA dyslipidemia inhibitor, there is a further step of administering a selected miRNA modulator to a cell, tissue, organ, or organism (collectively "biological matter") in need of treatment related to modulation of the targeted miRNA or in need of the physiological or biological results discussed herein. Consequently, in some methods there is a step of identifying a subject in need of treatment that can be provided by the miRNA modulator(s). It is contemplated that an effective amount of a miRNA modulator can be administered to an identified subject susceptible to such treatment in some embodiments. In particular embodiments, there is a therapeutic benefit conferred on the biological matter, where a "therapeutic benefit" refers to an improvement in the one or more conditions or symptoms associated with a disease or condition or an improvement in the prognosis, duration, or status with respect to the disease. It is contemplated that a therapeutic benefit includes, but is not limited to, a decrease in pain, a decrease in morbidity, or a decrease in a symptom. For example, with respect to dyslipidemia, it is contemplated that a therapeutic benefit can be inhibition of lipid accumulation in the blood, increased clearance of triglycerides in the blood stream, prevention of atherosclerosis, prevention of heart disease, inhibition of ANGPTL8 activity, or a combination thereof.

Furthermore, it is contemplated that the miRNA compositions may be provided as part of a therapy to a subject, in conjunction with traditional therapies or preventative agents. Moreover, it is contemplated that any method discussed in the context of therapy may be applied as a preventative measure, particularly in a subject identified to be potentially in need of the therapy or at risk of the condition or disease for which a therapy is needed.

A nucleic acid of a miRNA dyslipidemia inhibitor can enhance the effect or efficacy of another drug, reduce any side effects or toxicity, modify its bioavailability, and/or decrease the dosage or frequency needed. In certain embodiments, the other therapeutic drug is one or more of a statin, a fibrate, or a similar hyperlipidemia therapeutic. Consequently, in some embodiments, there is a method of treating a subject comprising administering to the subject a therapeutic and an effective amount of a miRNA molecule that improves the efficacy of a second therapeutic or protects non-targeted cells from a detrimental effect of a drug. Therapies also include a variety of combination therapies with both chemical and radiation based treatments. Combination therapies include but are not limited to, for example, one or more of statins, fibrates, Ezetimibe, or any analog or derivative variant of the foregoing.

Combination Treatments

In certain embodiments, the present compositions and methods involve a miRNA, or miRNA inhibitor, or expression construct encoding such. These miRNA compositions can be used in combination with a second therapy to enhance the effect of the miRNA therapy, or increase the therapeutic effect of another therapy being employed. These compositions would be provided in a combined amount effective to achieve the desired effect, such as to reduce a subject's circulating triglyceride levels. This process may involve contacting the cells with the miRNA or second therapy at the same or different time. This may be achieved by contacting the cell with one or more compositions or pharmacological formulation that includes or more of the agents, or by contacting the cell with two or more distinct compositions or formulations, wherein one composition provides (1) miRNA; and/or (2) a second therapy. A second composition or method may be administered that includes a satin, a fibrate, a combination thereof, or the like.

It is contemplated that one may provide a subject with the miRNA therapy and the second therapy within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. It is further contemplated that one may provide a subject with the miRNA therapy and the second therapy simultaneously, or one of the miRNA therapy and the second therapy may be provided in a first step involving one of the therapies and a second step involving the other therapy. The first step and the second step may be administered close in time, or remotely.

Further, when administering a combination therapy, the miRNA therapy and the second therapy may be administered together in a single composition, or separately as different compositions. That is to say, the miRNA therapy and the second therapy may be administered as a fixed or a free combination.

In certain embodiments, a course of treatment will last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days or more. It is contemplated that one agent may be given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, any combination thereof, and another agent is given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, or any combination thereof. Within a single day (24-hour period), the patient may be given one or multiple administrations of the agent(s). Moreover, after a course of treatment, it is contemplated that there is a period of time at which no treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

Various combinations may be employed, in the following non-limiting examples a miRNA therapy is "A" and a second therapy is "B":

A/B/A B/A/B B/B/A A/A/B A/B/B B/A/A
A/B/B/B B/A/B/B B/B/B/A B/B/A/B A/A/B/B A/B/A/B
A/B/B/A B/B/A/A B/A/B/A B/A/A/B A/A/A/B B/A/A/A
A/B/A/A A/A/B/A

Administration of any compound or therapy to a patient will follow general protocols for the administration of such compounds, taking into account the toxicity, if any, of the vector or any protein or other agent. Therefore, in some embodiments there is a step of monitoring toxicity that is attributable to combination therapy. It is expected that the treatment cycles would be repeated as necessary. It also is contemplated that various standard therapies, as well as surgical intervention, may be applied in combination with the described therapy.

In specific aspects, it is contemplated that a second therapy, such as administration of a statin, a fibrate, a combination thereof, or the like, is employed in combination with the miRNA therapy, as described herein.

A further embodiment includes methods of stimulating triglyceride degradation in a subject or tissue comprising administering to a subject in need of such stimulation, in an amount sufficient to stimulate triglyceride degradation, one or more nucleic acid molecules comprising (a) a miRNA sequence that is at least 80%, 85%, 90%, 95%, 96%, 97%, 98%, 99% or 100% identical to at least one of SEQ ID NO. 1 or SEQ ID NO. 2. In further aspects of a miRNA dyslipidemia inhibitor the subject has, is at risk of developing, or is suspected of having dyslipidemia, hyperlipidemia, atherosclerosis, heart disease, or a combination thereof.

IV. Pharmaceutical Formulations and Delivery

Methods described herein include the delivery of an effective amount of a pharmaceutical composition comprising a miRNA or an expression construct encoding the same. An "effective amount" of the pharmaceutical composition, generally, is defined as that amount sufficient to detectably achieve a desired result, for example, to ameliorate, reduce, minimize or limit the extent of a disease or its symptoms. Other more rigorous definitions may apply, including elimination, eradication or cure of disease.

A. Administration

In certain embodiments, it is desired to inhibit ANGPTL8 activity, stimulate lipoprotein lipase activity, and thus stimulate triglyceride degradation, in order to provide a therapeutic benefit to a subject in need thereof. The routes of administration will vary, naturally, with the location and nature of the site to be targeted, and include, e.g., intradermal, subcutaneous, regional, parenteral, intravenous, intramuscular, intranasal, systemic, and oral administration and formulation. Direct injection, local injection, or injection into vasculature at a target site is specifically contemplated for target areas. Local, regional, or systemic administration also may be appropriate.

Multiple injections delivered as a single dose may comprise at total volume of about 0.1 ml to about 0.5 ml. Compositions of a miRNA dyslipidemia inhibitor may be administered in multiple injections to a targeted site. In certain aspects, injections may be spaced at approximately 1 cm intervals.

Continuous administration also may be applied where appropriate. Delivery via syringe or catheterization is contemplated. Such continuous perfusion may take place for a period from about 1-2 hours, to about 2-6 hours, to about 6-12 hours, to about 12-24 hours, to about 1-2 days, to about 1-2 weeks or longer following the initiation of treatment. Generally, the dose of the therapeutic composition via continuous perfusion will be equivalent to that given by a single or multiple injections, adjusted over a period of time during which the perfusion occurs.

Treatment regimens may vary as well and often depend on disease progression and health and age of the patient. The clinician will be best suited to make such decisions based on the known efficacy and toxicity (if any) of the therapeutic formulations.

Treatments may include various "unit doses." A unit dose is defined as containing a predetermined quantity of a therapeutic composition(s). The quantity to be administered, and the particular route and formulation, are within the skill of those in the clinical arts. A unit dose need not be administered as a single injection but may comprise continuous infusion over a set period of time. With respect to a viral component of a miRNA dyslipidemia inhibitor, a unit dose may conveniently be described in terms of μg or mg of miRNA or miRNA mimetic. Alternatively, the amount specified may be the amount administered as the average daily, average weekly, or average monthly dose.

miRNA can be administered to a patient in a dose or doses of about or of at least about 0.005, 0.05, 0.5, 1, 5, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 μg, ng, or mg, or more, or any range derivable therein. Alternatively, the amount specified may be the amount administered as the average daily, average weekly, or average monthly dose, or it may be expressed in terms of mg/kg, where kg refers to the weight of the patient and the mg as specified above.

B. Formulations for Administration

In some embodiments, the composition for the delivery of a miRNA or an expression construct encoding such or combinations thereof is formulated for systemic administration. However, the pharmaceutical compositions disclosed herein may also be administered topically, parenterally, subcutaneously, directly, intratracheally, intravenously, intradermally, intramuscularly, or even intraperitoneally.

Injection of nucleic acids may be delivered by syringe or any other method used for injection of a solution, as long as the nucleic acid and any associated components can pass through the particular gauge of needle required for injection. A syringe system has also been described for use in gene therapy that permits multiple injections of predetermined quantities of a solution precisely at any depth.

Solutions of the active compounds are typically sterile and must be fluid to the extent that easy syringability exists. The solutions must be sufficiently stable under the conditions of manufacture and storage and must be preserved against the contaminating action of microorganisms, such as bacteria and fungi. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

In certain formulations, a water-based formulation is employed while in others, it may be lipid-based. In particular embodiments, a composition comprising a miRNA or a nucleic acid encoding the same is in a water-based formulation. In other embodiments, the formulation is lipid based.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral, intralesional, and intraperitoneal administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject. Moreover, for human administration, preparations may meet sterility, pyrogenicity, general safety, and purity standards as required by the relevant government agency, such as the US FDA Office of Biologics standards.

The use of carriers for pharmaceutical active substances is well known in the art. Except insofar as any conventional media or agent is incompatible with the active ingredient, its use in the therapeutic compositions is contemplated. Supplementary active ingredients can also be incorporated into the compositions.

The nucleic acid(s) may be administered in a manner compatible with the dosage formulation, and in such amount as will be therapeutically effective. The quantity to be administered may depend on the subject to be treated, including, e.g., the aggressiveness of the disease, and the previous or other courses of treatment. Precise amounts of active ingredient required to be administered may depend on the judgment of the practitioner. Suitable regimes for initial administration and subsequent administration are also variable, but are typified by an initial administration followed by other administrations. Such administration may be systemic, as a single dose, continuous over a period of time spanning 10, 20, 30, 40, 50, 60 minutes, and/or 1, 2, 3, 4, 5, 6, 7, 8, 9, 10, 11, 12, 13, 14, 15, 16, 17, 18, 19, 20, 21, 22, 23, 24 or more hours, and/or 1, 2, 3, 4, 5, 6, 7, days or more. Moreover, administration may be through a time release or sustained release mechanism, implemented by formulation and/or mode of administration.

Corresponding miRNA sequences that can be used in the context of a miRNA dyslipidemia inhibitor include, but are not limited to, all or a portion of those sequences in the sequence listing provided herein, as well as the miRNA precursor sequence, or complement of one or more of these miRNAs.

Any embodiment of a miRNA dyslipidemia inhibitor involving specific miRNAs by name is contemplated also to include embodiments involving miRNAs whose sequences are at least 80, 81, 82, 83, 84, 85, 86, 87, 88, 89, 90, 91, 92, 93, 94, 95, 96, 97, 98, and 99% identical to the mature sequence of the specified miRNA. In other aspects, miRNA of a miRNA dyslipidemia inhibitor may include additional nucleotides at the 5', 3', or both 5' and 3' ends of at least, at most, or about 1, 2, 3, 4, 5, 6, 7, 8, 9, or 10 or more assitional nucleotides.

It is contemplated that any method or composition described herein can be implemented with respect to any other method or composition described herein and that different embodiments may be combined. It is specifically contemplated that any methods and compositions discussed herein with respect to miRNA molecules or miRNA may be implemented with respect to synthetic miRNAs. Typically, the synthetic miRNA is exposed to the proper conditions to allow it to become or function, at least in part, as a mature miRNA under physiological circumstances.

It is contemplated that any embodiment discussed herein can be implemented with respect to any method or composition of a miRNA dyslipidemia inhibitor, and vice versa. Any embodiment discussed with respect to a particular condition can be applied or implemented with respect to a different condition. Furthermore, compositions and kits of a miRNA dyslipidemia inhibitor can be used to achieve methods of a miRNA dyslipidemia inhibitor.

V. Kits

A further embodiment concerns kits containing compositions of a miRNA dyslipidemia inhibitor or compositions to implement methods of treatment using a miRNA dyslipidemia inhibitor. In some embodiments, the kits can be used to increase or inhibit the activity of one or more miRNA molecules. In certain embodiments, a kit contains, contains at least, or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more synthetic miRNA molecules or miRNA inhibitors, or any range and combination derivable therein. Said kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1x, 2x, 5x, 10x, or 20x or more, including all values and ranges there between.

Kits for using miRNA probes, synthetic miRNAs, non-synthetic, and/or miRNA inhibitors of a miRNA dyslipidemia inhibitor for therapeutic, prognostic, or diagnostic applications are included as part of a miRNA dyslipidemia inhibitor.

Any of the compositions or components described herein may be included in a kit. In a non-limiting example, reagents for isolating miRNA, labeling miRNA, and/or evaluating a miRNA population using an array, nucleic acid amplification, and/or hybridization can be included in a kit, as well as reagents for preparation of samples from a subject. The kit may further include reagents for creating or synthesizing miRNA probes or therapeutics. The kits will thus typically comprise, in suitable container means, an enzyme for labeling the miRNA by incorporating labeled nucleotide or unlabeled nucleotides that are subsequently labeled. In certain aspects, the kit can include amplification reagents. In other aspects, the kit may include various supports, such as glass, nylon, polymeric beads, magnetic beads, and the like, and/or reagents for coupling any probes and/or target nucleic acids. It may also include one or more buffers, such as pharmaceutical buffer, reaction buffer, labeling buffer, washing buffer, or a hybridization buffer, compounds for preparing the miRNA probes, and components for isolating miRNA. Other kits may include components for making a nucleic acid array comprising miRNA, and thus, may include, for example, a solid support.

Kits for implementing methods described herein are specifically contemplated. In some embodiments, there are kits for preparing miRNA for multi-labeling and kits for preparing miRNA probes and/or miRNA arrays. In these embodiments, the kits comprise, in suitable container means, 1, 2, 3, 4, 5, 6, 7, 8, 9, 10, 11, 12 or more of the following: (I) poly(A) polymerase; (2) unmodified nucleotides (G, A, T, C, and/or U); (3) a modified nucleotide (labeled or unlabeled); (4) poly(A) polymerase buffer; and, (5) at least one microfilter; (6) label that can be attached to a nucleotide; (7) at least one miRNA probe; (8) reaction buffer; (9) a miRNA array or components for making such an array; (10) acetic acid; (11) alcohol; (12) solutions for preparing, isolating, enriching, and purifying miRNAs or miRNA probes or arrays. Other reagents include those generally used for manipulating RNA, such as formamide, loading dye, ribonuclease inhibitors, and DNase.

In other embodiments, there are kits for preventing or treating dyslipidemia. In these embodiments, the kits comprise, in suitable container means, 1, 2, 3, 4, 5, 6, 7, 8, 9, 10, 11, 12 or more of the following: (1) a therapeutic composition comprising a miRNA dyslipidemia inhibitor, (2) syringes, (3) a vial, tube, bottle, or the like, (4) alcohol swabs, (5) instructions for administering the therapeutic composition to a subject in need thereof.

For any kit embodiment, including an array, there can be nucleic acid molecules that contain or can be used to amplify a sequence that is a variant of, identical to, or complementary to all or part of any of SEQ ID NO. 1 and SEQ ID NO. 2. Any nucleic acid discussed above may be implemented as part of a kit.

The components of the kits may be packaged either in aqueous media or in lyophilized form. The container means of the kits will generally include at least one vial, test tube, flask, bottle, syringe or other container means, into which a component may be placed, and preferably, suitably aliquotted. Where there is more than one component in the kit (labeling reagent and label may be packaged together), the kit also will generally contain a second, third or other additional container into which the additional components may be separately placed. However, various combinations of components may be comprised in a vial. The kits also will typically include a means for containing the nucleic acids, and any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent or buffer. It is envisioned that the solvent may also be provided in another container means. In some embodiments, labeling dyes are provided as a dried power. It is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 μg or at least or at most those amounts of dried dye are provided in kits of thea miRNA dyslipidemia inhibitor. The dye may then be resuspended in any suitable solvent, such as DMSO.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

The present kits will also typically include a means for containing the vials in close confinement for commercial sale, such as, e.g., injection and/or blow-molded plastic containers into which the desired vials are retained.

Such kits may also include components that facilitate isolation of the labeled miRNA. It may also include components that preserve or maintain the miRNA or that protect against its degradation. Such components may be RNase-free or protect against RNases. Such kits generally will comprise, in suitable means, distinct containers for each individual reagent or solution.

A kit will also include instructions for employing the kit components as well the use of any other reagent not included in the kit. Instructions may include variations that can be implemented.

The kits may also include one or more of the following: Control RNA; nuclease-free water; RNase-free containers, such as 1.5 ml tubes; RNase-free elution tubes; PEG or dextran; ethanol; acetic acid; sodium acetate; ammonium acetate; guanidinium; detergent; nucleic acid size marker; RNase-free tube tips; and RNase or DNase inhibitors.

It is contemplated that such reagents are embodiments of kits. Such kits, however, are not limited to the particular items identified above and may include any reagent used for the manipulation or characterization of miRNA.

The following examples illustrate the present teachings.

Example 1

Materials and Methods

HepG2 cells were obtained from American Type Culture Collection (Rockville, Md.) and cultured in Minimum Essential Medium (GiBCO) supplemented with 10% fetal bovine serum and penicillin/streptomycin. For transient transfection assays, cells (at about 80% confluence) were transfected with control vector miRNA-CMV or with an expression vector containing miRNA-103 (2 μg plasmid DNA/1 million cells) using lipofectamine reagent according to the manufacturer's recommended method (ThermoFischer Scientific). Cells were treated overnight with palmitic acid (125 μM) using FFA free Bovine Serum Albumin (BSA) as a control. Cellular extracts were used for western blot analysis.

Figure 2:
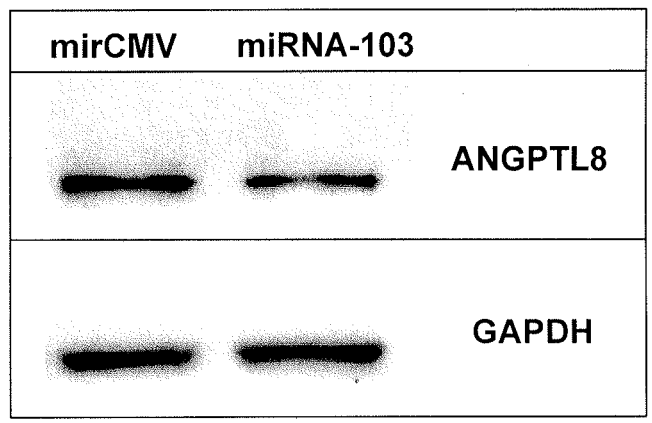
FIG. 2 depicts miRNA-103 binding and repression of ANGPTL8 expression compared to miRNA-CMV as a negative control.

Western blots were carried out using the transfected and treated HepG2 cellular extracts prepared in RIPA buffer (50 mM Tris-HCl pH 7.5, 150 mM NaCl, 1% Triton×100, 1 mM EDTA, 0.5% sodium deoxycholate and 0.1% SDS). Protein concentration was determined by the Bradford method using BSA as a standard. 20 tag of protein was resolved on 10% SDS-PAGE gels and proteins were transferred onto PVDF membranes. 5% non-fat dried milk in Tris-buffered saline containing 0.05% Tween 20 was used to block the membranes for 2 hours at room temperature. The membranes were then probed with a primary antibody (anti-ANGPTL8 R&D cat # MAB8548) overnight at 4° C. GAPDH (Millipore, Temecula, Calif.) was used as an internal control. After washing, the membranes were incubated with horseradish peroxidase-conjugated secondary antibody for 2 hours at room temperature. Finally, protein bands were visualized by chemiluminescence. The images were captured using the Versadoc 5000 system (Bio-Rad). For densitometric analysis, the intensity of the bands was determined using Quantity one Software (Bio-Rad). The results of this experiment are summarized in FIG. 2.

Figure 3:
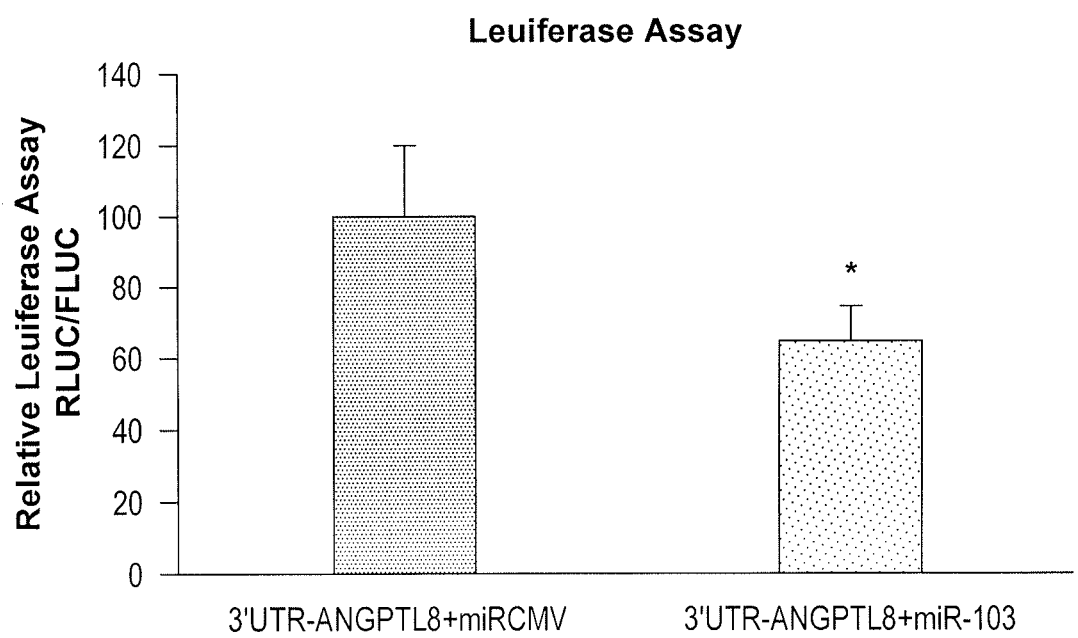
FIG. 3 depicts a luciferase binding assay demonstrating miRNA-103 binding to the ANGPTL8 3'UTR.
Figure 4A:
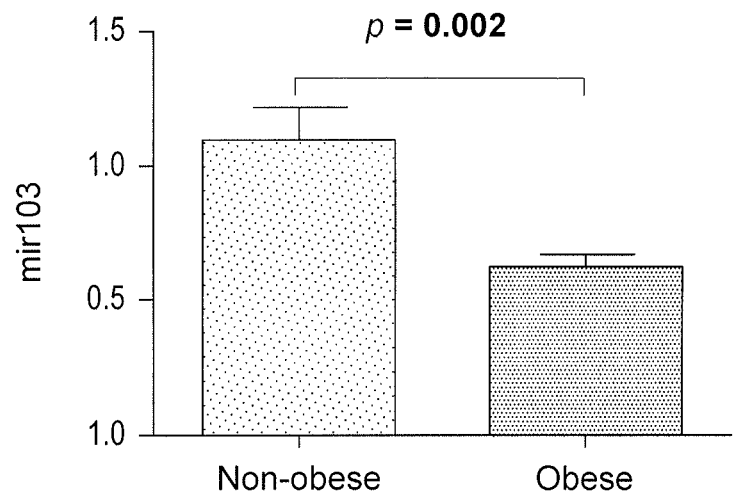
FIG. 4A depicts the negative correlation between miRNA-103 levels in circulating blood and obesity index.
Figure 4B:
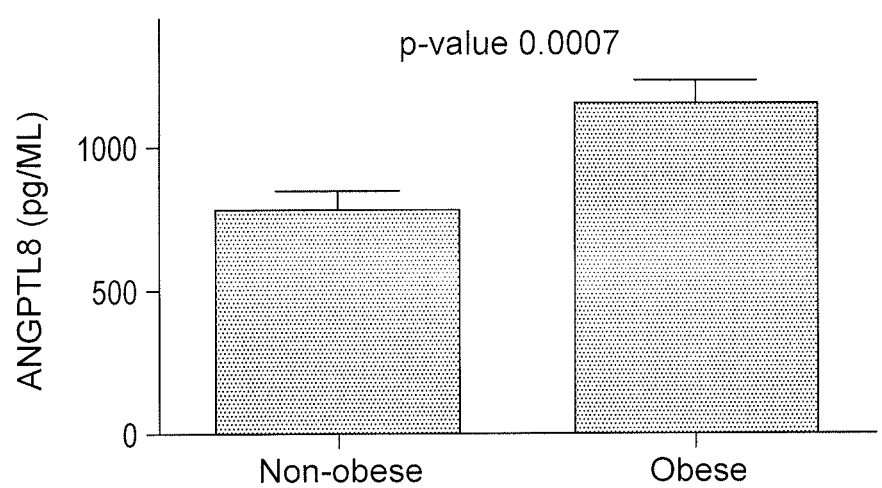
FIG. 4B depicts the positive correlation between ANGPTL8 levels in circulating blood and obesity index.
Figure 4C:
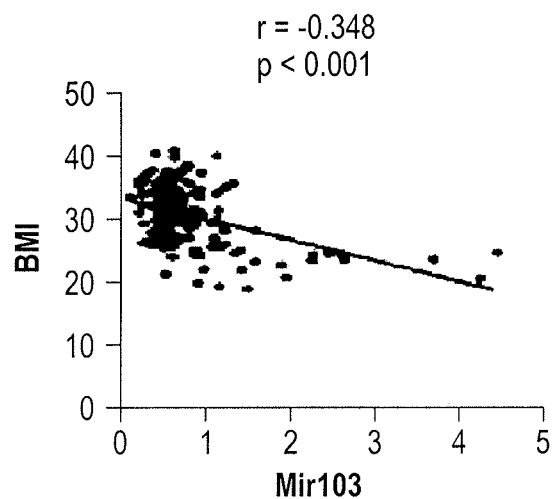
FIG. 4C depicts the negative correlation between miRNA-103 expression and BMI.
Figure 4D:
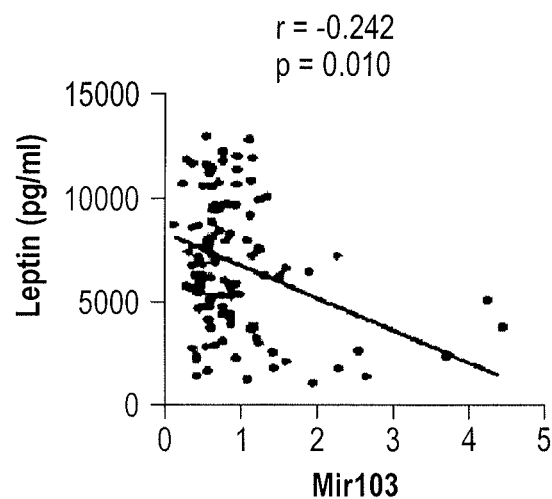
FIG. 4D depicts the negative correlation between Leptin in the blood stream and miRNA-103 expression.
Figure 4E:
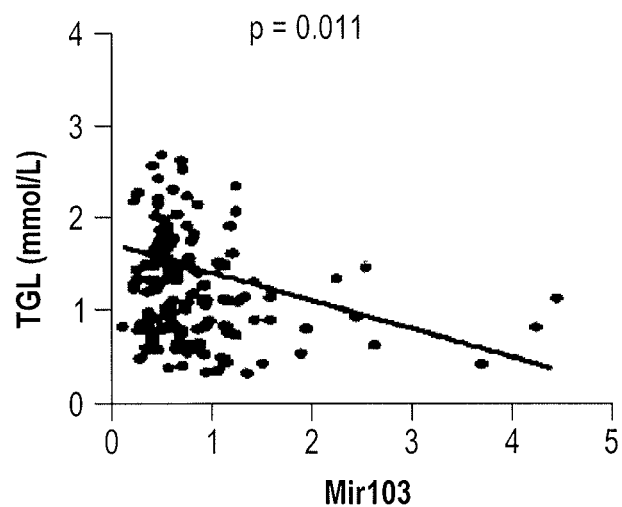
FIG. 4E depicts the negative correlation between triglyceride levels in the blood and miRNA-103 expression.

The Luc-Pair Duo-Luciferase Assay Kit 2.0 (GeneCopoeia) was used to validate predicted mRNA targets on 3'-UTRs. 3'-UTR clones of ANGPTL8 and pCMV6 were co-transfected with miRNA-103 and miRNA-CMV respectively in HEK293 and HepG2 cells. The luciferase assay was performed 24 hours after transfection. Cells were lysed using the lysis buffer provided in the Kit. Assay reagents and protocols were used as described in the Kit manual. Briefly, the assay was performed to detect and measure firefly luciferase (FLuc) and renilla luciferase (RLuc) sequentially, thus measuring the inhibitory effect of an miRNA on a target sequence. Luciferase activity was determined using a plate luminometer (SynergyH4). The results of these experiments are summarized in FIG. 3.

It is to be understood that the microRNA dyslipidemia inhibitor is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of inhibiting ANGPTL8 activity in a subject, comprising administering a therapeutic composition comprising miRNA-103 or a precursor thereof to said subject.

2. The method of claim 1, wherein administering the therapeutic composition comprising miRNA-103 prevents or treats a lipid metabolism disorder in the subject caused by the ANGPTL8 activity, the lipid metabolism disorder selected from the group consisting of hyperlipidemia, atherosclerosis, and heart disease.

3. The method of claim 1 wherein the therapeutic composition comprises SEQ ID NO. 1.

4. The method of claim 1 wherein the therapeutic composition comprises SEQ ID NO. 2.

5. The method of claim 1 wherein the miRNA-103 is a chemically modified miRNA.

6. The method of claim 1 wherein said therapeutic composition further comprises a delivery system.

7. The method of claim 6, wherein the delivery system is selected from the group consisting of liposomes, lipidoids, biodegradable polymers, and vesicles, and the miRNA-103 is encapsulated within the delivery system.

8. The method of claim 1, wherein the administering comprises injecting the therapeutic composition directly into a target tissue of the subject.

9. The method of claim 8, wherein the target tissue is liver tissue or adipose tissue.

\* \* \* \* \*